United States Patent [19]

Tulunay

[11] Patent Number: 6,110,954
[45] Date of Patent: Aug. 29, 2000

[54] TREATMENT

[76] Inventor: Cankat Tulunay, Gurgen Sok. No. 23, Erdemkent, Cay Yolu, Ankara, Turkey

[21] Appl. No.: 09/353,641

[22] Filed: Jul. 15, 1999

[30] Foreign Application Priority Data

Jul. 16, 1998 [GB] United Kingdom .................. 9815497

[51] Int. Cl.$^7$ ................................................ A61K 31/415
[52] U.S. Cl. ............................................................. 514/403
[58] Field of Search ............................................... 514/403

[56] References Cited

U.S. PATENT DOCUMENTS

| | | | |
|---|---|---|---|
| 5,331,000 | 7/1994 | Young et al. ........................... | 514/570 |
| 5,352,683 | 10/1994 | Mayer et al. . | |
| 5,502,058 | 3/1996 | Mayer et al. . | |
| 5,919,826 | 7/1999 | Caruso ................................... | 514/629 |

OTHER PUBLICATIONS

Alessandra Beirith, Adair R.S. Santos, Ana L.S. Rodrigues, Tania B. Creczynski–Pasa, and Joao B. Calixto, "Spinal and SupraspinalAntiociceptive Action of Dipyrone in Formalin, Capsaicin and Glutamate Tests. Study of the Mechanism of Action", European Journal of Pharmacology (1998).

Joseph F. Antognini, MD., "Intrathecal Acetylsalicylic Acid and Indomethacin are not Analygesic for a Supramaximal Stimulus", International Anesthesia Research Society, 1993.

M. Pellerin, F. Hardy, A. Abergel, D. Boule, J.H. Palacci, P. Babinet, L. NG Wingtin, J. Glowinski, J.–F. Amiot, D. Mechali, N. Colbert, M. Starkman, "Chronic Refractory Pain in Cancer Patients" La Presse Medicale, Sep. 19, 1987.

F. Molke Jensen, J.B. Dahl and C. Frigast, "Digest Spinal Effect of Intrathecal Acetaminophen on Visceral Noxious Stimulation in Rabbits" Acta Anaesthesiol Scand 1992.

Martindale The Extra Pharmacopoeia 30$^{th}$ Edition 1993 p. 13.

*Primary Examiner*—Theodore J. Criares
*Assistant Examiner*—Jennifer Kim
*Attorney, Agent, or Firm*—Bacon & Thomas

[57] ABSTRACT

The use of a non-acidic non-steroidal anti-inflammatory drug (NSAID) such as dipyrone in the manufacture of a medicament for use in the treatment of pain in humans by epidural or intrathecal injection.

7 Claims, No Drawings

TREATMENT

This invention is concerned with the treatment of pain in humans and in particular the treatment of severe pain with non-steroidal anti-inflammatory drugs (NSAIDs) by epidural or intrathecal injection.

NSAIDs such as aspirin are widely used in the treatment of mild or moderate pain. They are also used in the management of moderate or severe pain to potentiate the effects of opioids, and they can also be used for acute or chronic pain. Some NSAIDs have been formulated for injection by the intravenous and intramuscular routes. However, in the treatment of severe acute or chronic pain it is usually necessary to use a strong opioid such as morphine. Drugs of this kind are very effective and can be administered by a number of routes, such as the oral route, intravenous or intramuscular injection and epidural or intrathecal injection, but they can produce undesirable adverse effects such as sedation, nausea, vomiting, constipation, respiratory depression and dependency.

A number of non-opioid drugs have been suggested for use by epidural or intrathecal injection, but these methods have not been adopted in actual practice to any great extent. NSAIDs have not been used or suggested for use in humans in this way and their molecular structure and properties generally make them unsuitable for this type of application.

It is the objective of this invention to provide a method for the treatment of pain in humans by the epidural or intrathecal route which does not use an opioid drug and hence avoids the adverse effects of such drugs. We have thus found that some non-acidic NSAIDs can be used successfully by these routes and can either replace the use of opioids or supplement them, allowing the opioid dose to be reduced.

The invention is thus a method for the treatment of pain in humans in which a non-acidic NSAID is administered by epidural or intrathecal injection. The invention also provides the use of a non-acidic NSAID in the manufacture of a medicament for use in the treatment of pain in humans by epidural or intrathecal injection.

The non-acidic NSAID should be a compound capable of being formulated for injection as a neutral solution or a substantially neutral solution. Such compositions do not have an irritating effect on the spinal cord and may be formulated in conventional manner as aqueous solutions for injection. Dipyrone (metamizole) is the preferred NSAID and is available as ampoules in a suitable injectable form under the trade name Novalgin (Hoechst Marion Roussel). Dipyrone is a sodium salt and other salts of the same active constituent can also be used, for example other alkali metal or alkaline earth metal salts such as metamizole magnesium and metamizole calcium. Other non-acidic NSAIDs which may be used include acetaminophen (paracetamol) and lysine acetylsalicylate.

The NSAID can be administered as a single dose which can vary substantially depending on the age, weight and condition of the patient and the pain condition to be treated and will usually be in the range 100–3000 mg. In our studies using dipyrone we have for example used single doses of 100 or 500 to 1000 mg, usually 1 g. The NSAID can also be administered as an intermittent infusion for patient-controlled analgesia.

The types of pain that can be treated include all types of chronic and acute pain, post-operative pain and cancer pain. NSAIDs may also be used in addition to epidurally administered opiates (morphine etc.), to reduce the dose and side effects of opiates; during childbirth, for the prevention of pain (the epidural use of opiates during childbirth presents risks for the mother and the baby); and during operations for preemptive analgesia. Other applications include the treatment of leg pain such as in Burger disease, caused by peripheral artery malfunctions; in other forms of leg pain, for the improvement of peripheral blood circulation, using both the epidural and intratracheal methods; and for pain associated with strokes and cerebral spasm.

In our studies on a number of patients we have for example found:

1. For the management of pain, 100–1000 mg of epidural dipyrone has produced analgesia for 6–12 hours.
2. In terminal cancer patients who have become addicted to morphine, 500–1000 mg epidural dipyrone produces analgesia for 6–24 hours. 2–3 mg of morphine produces only light analgesia to these patients and the duration is only 1–2 hours.
3. Using the epidural method:
   a) patients have been using less opioid with fewer side effects,
   b) the pain and suffering of patients who are not affected by morphine and other opioids can be reduced, and
   c) it will now be possible to manage other kinds of pain (intractible pain, phantom pain, shingles pain) and during birth.

Our studies in terminal cancer patients and Burger patients are described in more detail below.

The analgesic effect of epidural dipyrone in terminal cancer patients was investigated in groups of six patients using 1 g single doses of Novalgin. The patients reported a reduction of pain to a level of approximately 50% over the first 45 minutes after administration. This level of pain reduction was maintained until about 2 hours after administration and then the pain rose to about the 40% reduction level 3 hours after administration. Essentially the same results were observed using a visual analog scale. After 6 hours, 17% of patients reported a good analgesic effect, 17% a medium effect and 66% a slight effect.

The analgesic effect of epidural dipyrone in Burger patients was investigated in a group of nine patients, again using 1 g single doses of Novalgin. The effect was monitored by measuring the changes in blood flow in two arteries in both the patients and in a control group and also in comparison with lidocaine. In the arteria tibialis, dipyrone increased the blood flow by about 2 ml/sc in the patients and by about 14 ml/sc in the control group, whereas lidocaine reduced the flow by about 16 ml/sc in the patients and by about 2 ml/sc in the control group. In the arteria dorsalis pedis, dipyrone increased the blood flow by about 5 ml/sc in the patients and by about 10 ml/sc in the control group, whereas lidocaine reduced the flow by about 18 ml/sc in the patients and by about 2 ml/sc in the control group.

What is claimed is:

1. A method for the treatment of pain in humans by epidural or intrathecal injection of an effective amount of a non-acidic non-steroidal anti-inflammatory drug (NSAID) dipyrone.

2. The method of claim 1 in which the medicament is a neutral or sustantially neutral solution of the NSAID.

3. The method of claim 1 in which the dose of dipyrone to be administered is 500–1000 mg.

4. The method of claim 1 in which the pain to be treated is chronic or acute pain.

5. The method of claim 4 in which the pain is cancer, post-operative or childbirth pain.

6. A method for the alleviation of chronic or acute pain in humans in which an effective amount of dipyrone is administered by epidural or intrathecal injection to replace or supplement the use of morphine or other opioid drug.

7. The method of claim 6 in which said pain is cancer, post-operative or childbirth pain.

* * * * *